United States Patent
Koeth et al.

(10) Patent No.: US 11,058,831 B2
(45) Date of Patent: Jul. 13, 2021

(54) INSUFFLATION HOSE FOR USE IN LAPAROSCOPY WITH HEATING ELEMENT, HUMIDIFYING MEDIUM, AND DEVICE FOR DETERMINING THE MOISTURE CONTENT

(71) Applicant: W.O.M. World of Medicine GmbH, Berlin (DE)

(72) Inventors: Yves Koeth, Berlin (DE); Felix Menzel, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 206 days.

(21) Appl. No.: 15/560,220

(22) PCT Filed: Mar. 16, 2017

(86) PCT No.: PCT/DE2017/000068
§ 371 (c)(1),
(2) Date: Aug. 24, 2018

(87) PCT Pub. No.: WO2017/157365
PCT Pub. Date: Sep. 21, 2017

(65) Prior Publication Data
US 2018/0369510 A1 Dec. 27, 2018

(30) Foreign Application Priority Data
Mar. 16, 2016 (DE) .................. 10 2016 003172.7

(51) Int. Cl.
*A61M 13/00* (2006.01)
*A61M 16/16* (2006.01)
*G01F 1/69* (2006.01)
*A61M 16/10* (2006.01)

(52) U.S. Cl.
CPC .......... *A61M 13/003* (2013.01); *A61M 16/16* (2013.01); *A61M 16/109* (2014.02);
(Continued)

(58) Field of Classification Search
CPC .. A61M 13/003; A61M 16/16; A61M 16/109; A61M 2205/18;
(Continued)

(56) References Cited

U.S. PATENT DOCUMENTS 2,814,948 A * 12/1957 Neel, Jr. ................ G01N 25/56
73/170.16
4,708,831 A 11/1987 Elsworth et al.
(Continued)

FOREIGN PATENT DOCUMENTS

DE 3617031 A1 12/1986
DE 19510710 A1 9/1996
(Continued)

OTHER PUBLICATIONS

Rolf Isermann, "Mechatronic Systems" 2nd edition, chapter 7.2 "Parameter Estimation for Discrete Time Signals", 9 pages, copyright 2005, in both German and English.

*Primary Examiner* — Nathan R Price
*Assistant Examiner* — Dung T Ulsh
(74) *Attorney, Agent, or Firm* — Mayer & Williams, PC; Stuart H. Mayer

(57) ABSTRACT

The present invention relates to an insufflator comprising an insufflation hose with an integrated heating element and a humidifying medium for use in laparoscopy, wherein the heating wire is adapted to measure the resistance and permits a refill alarm.

7 Claims, 4 Drawing Sheets

(52) U.S. Cl.
CPC . *A61M 2205/18* (2013.01); *A61M 2205/3379* (2013.01); *A61M 2205/3653* (2013.01); *A61M 2205/6018* (2013.01); *A61M 2210/1021* (2013.01); *G01F 1/69* (2013.01)

(58) Field of Classification Search
CPC .. A61M 2205/3379; A61M 2205/3653; A61M 2205/6018; A61M 2210/1021
See application file for complete search history.

(56) References Cited

U.S. PATENT DOCUMENTS

| | | | |
|---|---|---|---|
| 2003/0181857 A1 | 9/2003 | Blake et al. | |
| 2013/0211282 A1* | 8/2013 | Bunch | A61B 18/1815 600/549 |
| 2013/0255670 A1* | 10/2013 | Ott | A61M 16/16 128/200.14 |
| 2016/0041025 A1* | 2/2016 | Haynes | G01F 23/72 73/1.73 |

FOREIGN PATENT DOCUMENTS

| | | |
|---|---|---|
| DE | 10 2013 000489 A1 | 7/2014 |
| DE | 10 2013 000492 A1 | 7/2014 |
| WO | 2013/137753 A1 | 9/2013 |
| WO | 2014/111083 A1 | 7/2014 |
| WO | WO 2014111083 * | 7/2014 ........... A61B 1/3132 |
| WO | WO-2014111083 A1 * | 7/2014 ........... A61B 1/3132 |
| WO | 2015/027980 A2 | 3/2015 |
| WO | 2015/135040 A1 | 9/2015 |

\* cited by examiner

INSUFFLATION HOSE FOR USE IN LAPAROSCOPY WITH HEATING ELEMENT, HUMIDIFYING MEDIUM, AND DEVICE FOR DETERMINING THE MOISTURE CONTENT

FIELD

The present invention relates to an insufflator comprising an insufflation hose with an integrated heating element and a humidifying medium for use in laparoscopy, wherein the heating wire is adapted for measuring the resistance and permits a refill alarm.

BACKGROUND

Laparoscopy is a medical intervention, in which the abdominal cavity and the organs therein can visually be inspected. For this purpose, usually, small skin incisions (0.3 to 2 centimeters) are made in the abdominal wall, and a trocar is introduced therethrough, which in turn can accommodate an optical device. By using a special endoscope (laparoscope), the abdomen can be inspected. In diagnostic laparoscopy, the abdomen is visually inspected only, in therapeutic laparoscopy, surgical interventions can also be carried out.

Usually, at the beginning of a laparoscopy, first the abdomen is filled with gas, in order to create a pneumoperitoneum. Various gases have already been used for this purpose, such as air, nitrogen, or carbon dioxide ($CO_2$). The use of carbon dioxide gas has proved to be particularly effective. It was found that it is reasonable, in particular with longer laparoscopic interventions, on one hand to heat the introduced gas, and on the other hand to moisten it. Heating the gas serves for that the patient is not cooled down, and that a diffuse feeling of pain of the patient is avoided, which is likely a consequence of local cooling due to the entry of a cold gas.

Moistening serves for that drying of the inner abdominal surface is prevented, in order to avoid the cooling effect associated therewith.

For this purpose, prior art already provides suggestions. For instance, the German patent specification DE 19510710 describes a device that provides a means for adjusting the moisture of the gas (for example a sponge) and that optionally may comprise an additional heating element.

The DE 10 2013 000492 A1 describes a hose comprising an integrated heating element for use in laparoscopy, which simultaneously contains a humidifying medium. According to this document, before a surgery, the humidifying medium is moistened with water. Depending on the water absorption of the material described therein, the volumetric gas flow and the duration of the surgical operation, intra-operatively a re-humidification of the humidifying medium may be necessary. Since the evaporation rate of the water depends on a number of parameters, it can up to now only be estimated when a refill is required. Alternatively, variants are described that provide a moisture sensor for detecting the moisture of the gas in the gas channel. This has, however, several drawbacks. On the one hand, the moisture sensor has to be connected electrically, thus the design of the filter interface being more complicated. Furthermore, the moisture sensor represents a non-negligible flow resistance in the gas channel. This will lead to a lower flow rate not being in agreement with the current flow requirements.

Another device for moistening gases in medical engineering is described in the DE 3617031 A1 (priorities: NZ 21263, NZ 215123, and NZ 214694). In a complex hose system, a hose being always filled with water is provided. Through a microporous hose wall, water vapor is transferred to the gas. A sensor monitors the water temperature.

It is the object of the present invention to determine the condition of the humidifying medium in relation to its water content, i.e. the water content of the humidifying medium, without implementing the above drawbacks. The primary object is the generation of a refill alarm/signal, i.e. of a signal, which informs the user, when a refill of water is required. In the present invention, the terms "water content of the humidifying medium" and "moisture of the humidifying medium" are considered as synonymous.

SUMMARY

The solution of this object is achieved by the subject matter of the patent claims, i.e., an insufflation device comprising an insufflation hose that in turn comprises a heating and humidifying device. Measuring the water content of the humidifying medium occurs by evaluating the measurement of the resistance of the heating wire.

Therefore, the invention relates to an insufflation device for use in medical engineering, including
- an insufflator for gas supply and an insufflation hose, the insufflation hose including in its interior a humidifying material,
- the humidifying material being in contact with a heating element,
- the heating element being activatable by applying a current,
- the heating element consisting of a wire, the wire changing its resistance with varying temperature,
characterized by that
- the insufflator includes a device for measuring the wire resistance, and
- that the insufflator further includes a computing device that determines the water content of the humidifying material from the measured change in resistance of the heating wire during the heating process.

As described above, first of all, the device according to the invention includes an insufflator and a heating hose. The heating hose is designed according to the teaching of the DE 10 2013 000492 A1, i.e., in the interior of the hose is provided a humidifying material, and in the immediate neighborhood thereof is located a heating element. The heating element consists of a heating wire that in a preferred manner has the form of a wire helix. This heating wire may be situated in the interior of the hose. An alternative embodiment is that the heating wire is embedded in the hose wall. The heating wire usually has a length of 50 centimeters to 10 meters. The wire diameter is typically 0.25 to 2 millimeters. In this way, a heating power of 5 to 50 watts can be achieved. When the wire is positioned in the interior of the hose, then it has in a preferred manner a shape of a helix with a diameter from 3 to 4 millimeters.

In the immediate neighborhood of the heating element, in a preferred manner being in direct contact, a humidifying material is positioned. This is a porous material, which is capable of absorbing a liquid, in particular water. This humidifying material for example encloses the wire helix mentioned above. In case that the wire is embedded in the hose wall, it is preferred that the humidifying material is in direct contact with the hose wall. As a humidifying material, in the simplest case, sterile cotton can be used, which is capable of absorbing a certain amount of water. Alternatively, sponges, super-absorbing polymers (SAP), blotting paper, or a material consisting of phenolic resins can be used. Alternative embodiments are possible.

It is crucial for the use according to the invention that for the heating wire a material is used, the resistance of which varies with the temperature. Such a change in resistance with varying temperature of the heating wire is physically defined by the temperature coefficient. Desirable for the heating wire is a material, for which the resistance between 0 and 100 degrees Celsius increases linearly with the temperature, and wherein the increase is sufficiently measurable. When the temperature coefficient of the material is not linear, the evaluation becomes more complicated, is nevertheless feasible. Desirable is an increase in resistance in the mentioned temperature range of 0.1 ohm/K. Such materials are for example iron, nickel or alloys thereof. Such products are available on the market and need no further explanation here. Typical heating wires for the use according to the invention have a resistance from 2 to 30 ohms/m and have a diameter from 0.25 to 2 millimeters. For those skilled in the art it is obvious that this composition of the wire and its diameter must be as constant as possible over the entire length.

Such a heating wire of e.g. 6 meters length and a resistance of 3 ohms/m can be integrated in a hose of 3 meters length. When the power of the wire per meter is higher or lower (due to a differing resistance value), the required heating power can be varied by modifying the wire length.

The use of such a wire permits, as described in the DE 10 2013 000489 A1, to measure the temperature of the wire without an additional transducer. For this purpose, the resistance of the wire is measured and the wire temperature is calculated therefrom. Examples thereof are given in the mentioned document DE 10 2013 000489 A1.

In order to determine the water content of the humidifying medium, according to the invention, the resistance behavior over time of the heating wire during the heating process is evaluated. Due to the different properties of the heating system with a wet humidifying medium compared to a dry humidifying medium, the time characteristics of the change in resistance of the heating wire vary as a consequence of an electrical excitation. This behavior can be analyzed in the heating phase of a heating period as well as in a cooling phase of a heating period, in order to determine the water content. The resistance of the heating wire increases depending on the water content of the humidifying medium as a consequence of an excitation in a different speed and in a different strength. With a suddenly occurring and thereafter persisting constant heating power, the heating wire reaches, after a certain time depending on the moisture of the system, a thermal equilibrium, such that the resistance will not further increase after expiration of this "heating-up time". The value $T_{100}$ describes the time constant of the heating system, which corresponds to the time in which 100% of the stationary final value are achieved. In the simplest case, the measurement of this time $T_{100}$ for achieving this stationary final value can be used as an indication of the water content. If, starting from this stationary final value, the heating power is suddenly deactivated again, the system will return to its original condition, with the "cooling-down time" for achieving this original condition from the time of the deactivation of the heating system also being dependent on the degree of moisture. Under identical conditions, this time also corresponds to the time $T_{100}$.

DETAILED DESCRIPTION

Until the thermal equilibrium is achieved, different times may pass. Therefore, it may be reasonable to also determine the degree of humidity from short and differently long "heating pulses" that occur, e.g., with a control procedure using a two-point controller. For this purpose, for example, the rate of change in resistance over time could be evaluated. This method is however prone to errors, since this rate of change depends on various factors, e.g., the heating power, and since for a control process, it cannot be guaranteed that the heating power always has a certain value. Furthermore, the rate of change in resistance is not constant in different time periods during heating-up or cooling-down, as shown in the curves in FIG. 1, such that precise "trigger points" need to be defined.

In the following, another method according to the invention is described that allows arbitrarily short heating-up and cooling-down phases and can determine the degree of humidity in a sufficiently precise and error-tolerant manner. The method consists in that the courses over time of the wire resistance as a function of the excitation over time are described by a model, and that the parameters of this model for the elapsed time are identified.

For this purpose, the model includes the excitation as well as the resistance of the wire. This model may, e.g., be a linear differential equation of first order:

$$T_{63} \cdot \dot{R} + R_H(t) + K \cdot S_H(t)$$

$R_H$=resistance of the heating wire
K=amplification factor
$S_H$=condition of the heating system (ON/OFF)

Figure 1:
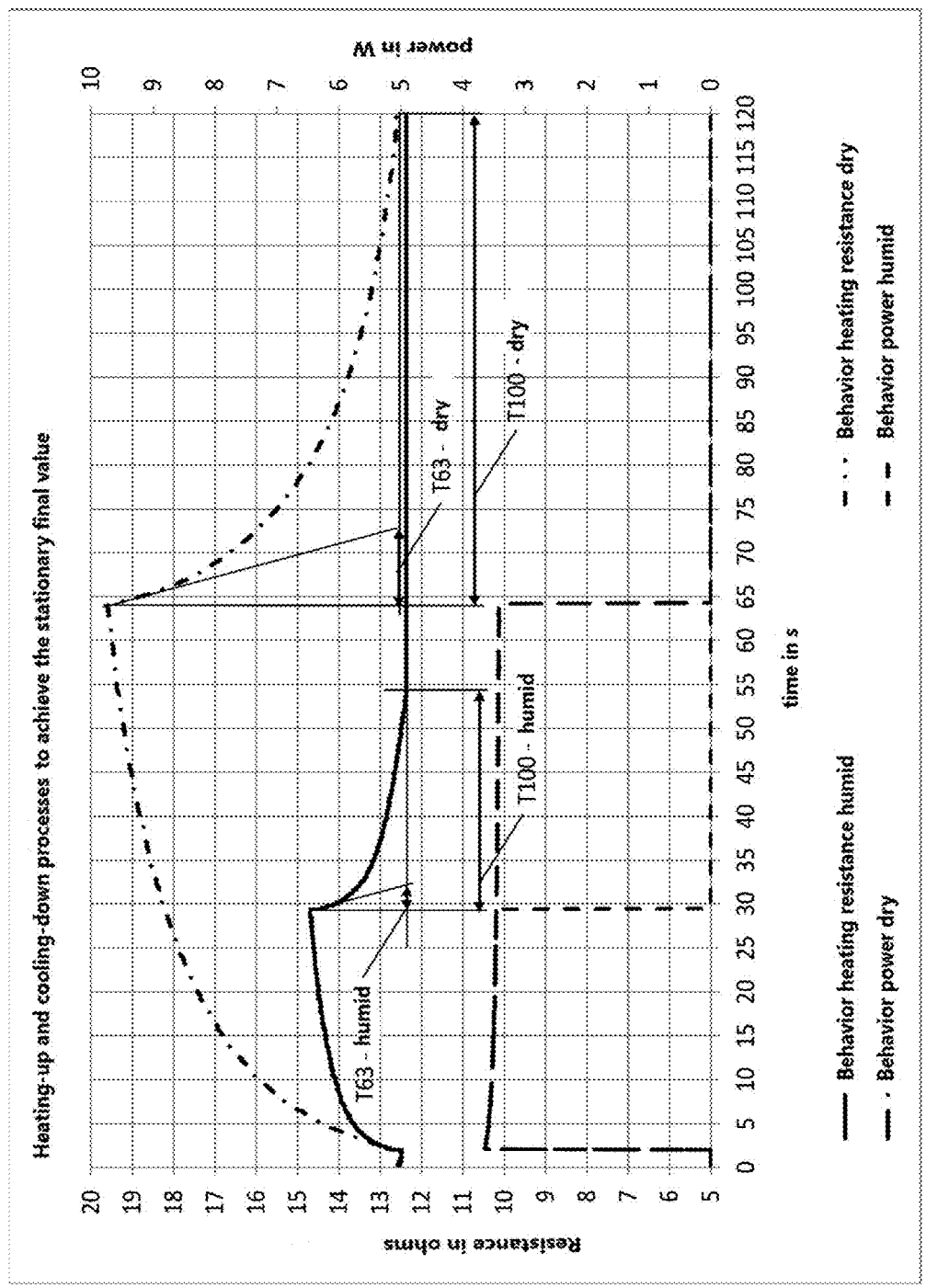
FIG. 1 shows a comparison of the heating-up and cooling-down processes to achieve the stationary final value for a wet and a dry humidifying medium.
Figure 2:
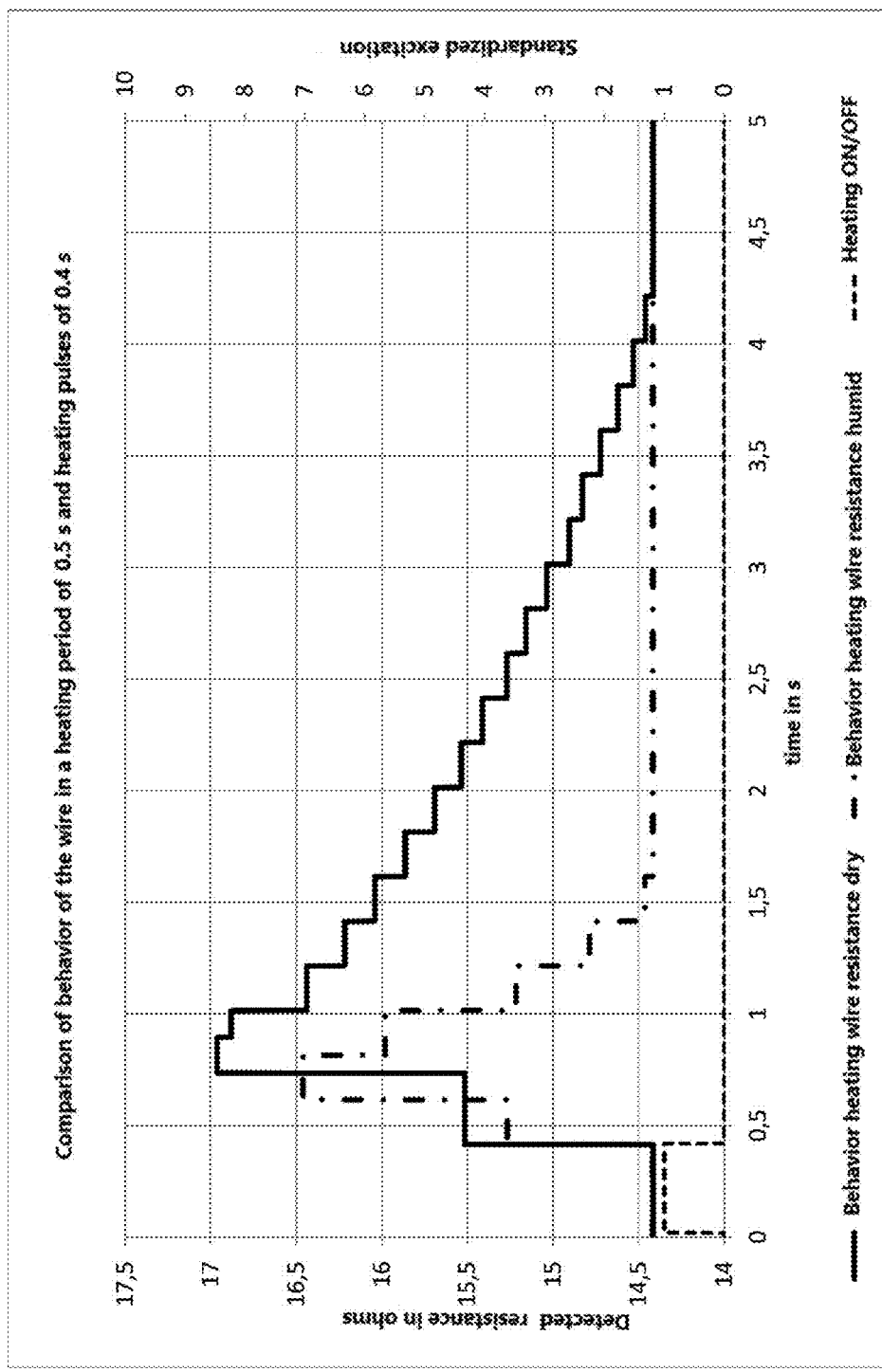
FIG. 2 shows a comparison of the change in wire resistance for short heating pulses with a wet and dry humidifying medium.
Figure 3:
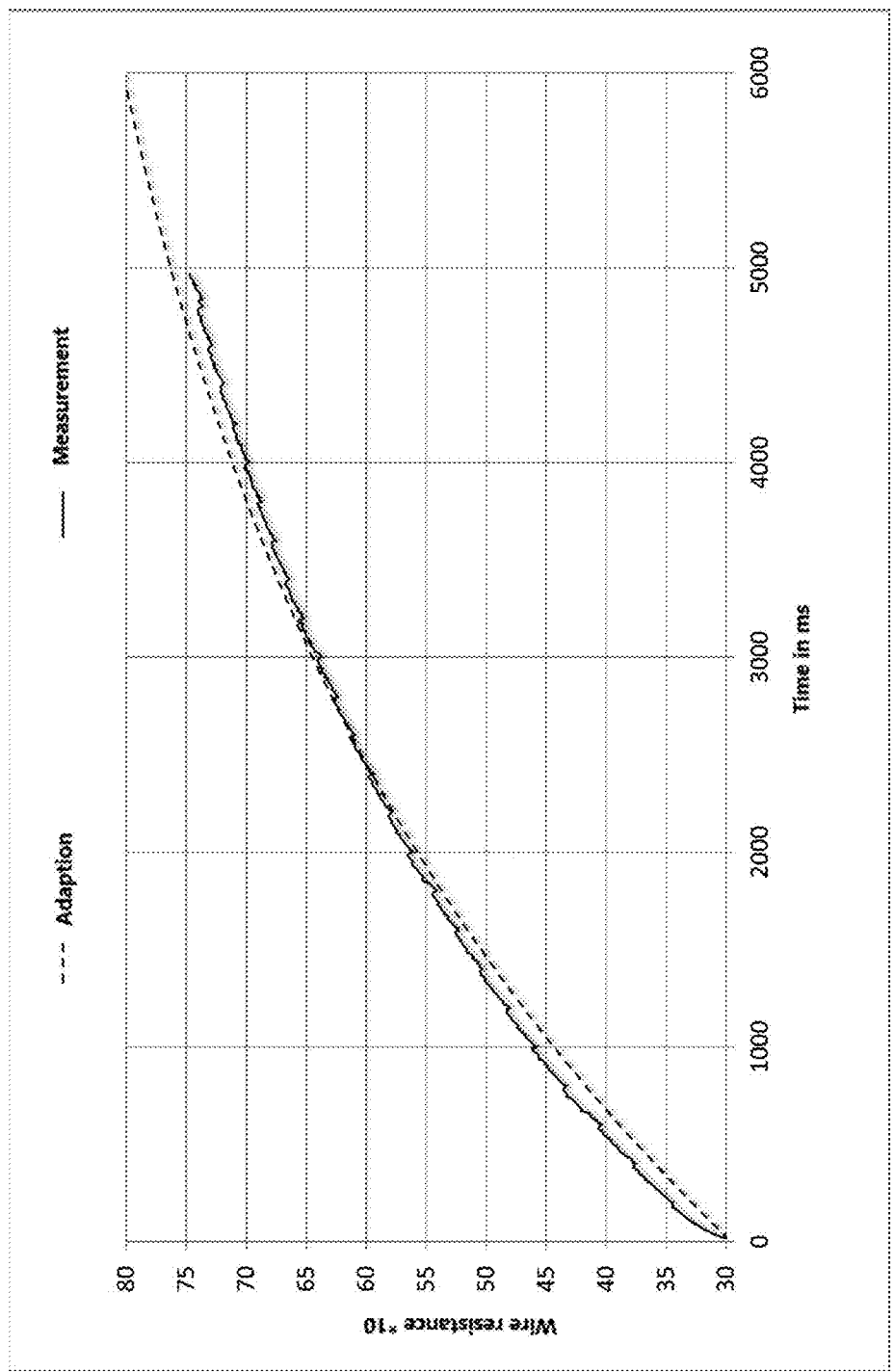
FIG. 3 shows the adjustment of the model to the measurement within 5 s.
Figure 4:
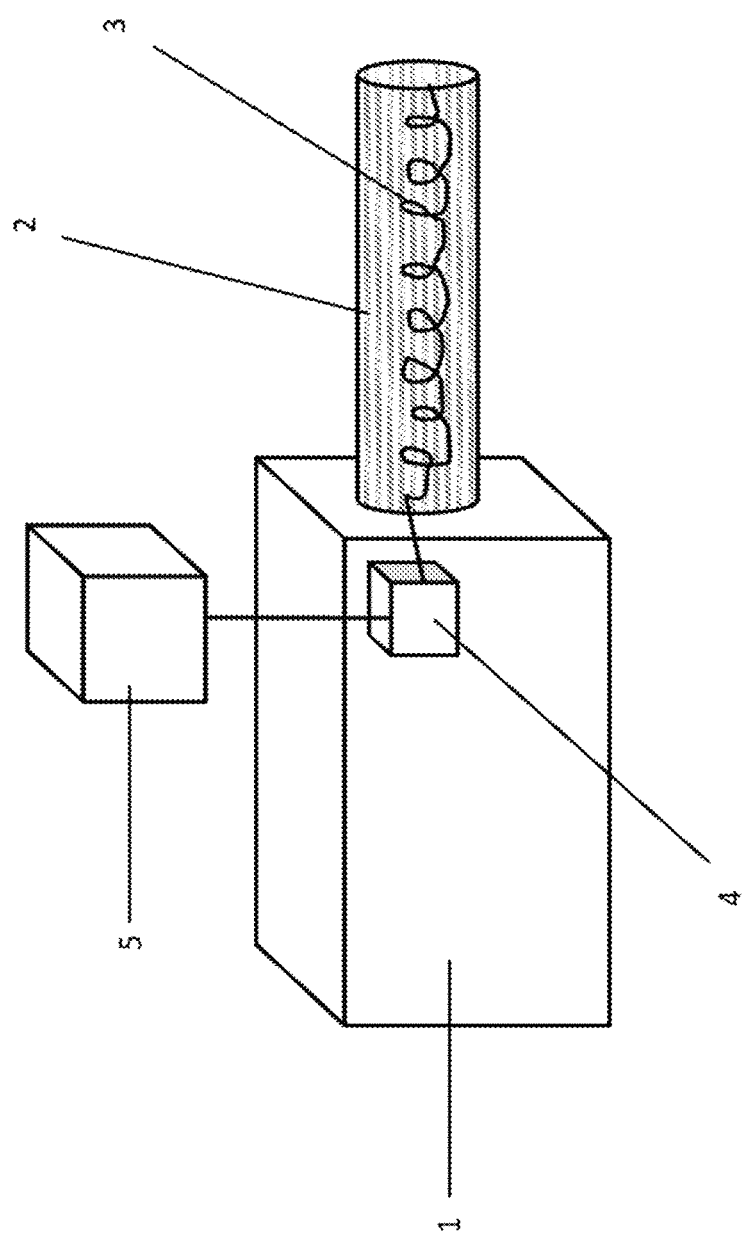
FIG. 4 shows an insufflator (1) with an insufflation hose (2) including in its interior a humidifying material, a heating element consisting of a wire (3), the wire changing its resistance with varying temperature, a device (4) for measuring the wire resistance and a computing device (5) determining the water content of the humidifying material from the measured change in resistance of the heating wire.

In the model, $T_{63}$ describes the time constant of the heating system, which, provided that the model is applicable, corresponds to the time in which 63% of the stationary final value have been achieved. The parameter K describes the so-called stationary amplification. With a suitable algorithm, e.g., a recursive "least squares method", a discrete formu-lation of this model can be adjusted to the detected measurement values of the excitation and of the wire resistance by the step-wise optimization of the parameters $T_{63}$ and K. In a way similar to the calculation of a moving average, this algorithm can be applied during the elapsed time to measured curves, as shown in the examples of FIG. 1 or FIG. 2. More detailed information about parameter identification of linear systems can be found, e.g., in Isermann, "Mechatronische Systeme Grundlagen", 2nd edition, chap-ter 7.2 "Parameterschätzung für zeitdiskrete Signale (Parameter Estimation for Time-discrete Signals)", p. 339-343.

By the described method, the determination of $T_{63}$ is also possible for short dynamic time courses, such as shown FIG. 2, and thus a conclusion with regard to the water content of the humidifying medium is possible.

The values of $T_{63}$ for the determination of the water content according to the described method depend on the precise hose specification. It makes sense, therefore, to measure every different embodiment of a hose according to the invention, and to then base the adjustment of the insufflator on the measured values. As already described in the document DE 10 2013 000489 A1, the adjustment of the heating power to the actual requirement (depending on outside temperature and volumetric gas flow) occurs by extending or reducing the heating cycles. For the use according to the invention, therefore, it may be necessary to define special measurement cycles for measuring the degree of moisture of the humidifying medium and to shortly intervene in the described control process. For example, a five-second heating phase with precisely defined heating power may occur once a minute in a separate measurement interval. Other configurations of the measurement cycles are easily conceivable. Analogous to the description in the DE 10 2013 000489 A1, it is of course possible to measure the precise characteristics of the individual heating hose (temperature coefficient in the range from 0 to 100 degrees Celsius, dependence of the gas temperature at the hose exit on heating power and volumetric gas flow, heating-up rates as a function of the moisture of the humidifying medium) during production of the hose and to store them in a flash memory that is (for example) positioned at the machine-side hose connection. Thus, when connecting the hose to the insufflation device, for example, the data can be transmitted to the device and provided for further use. For a clinical application, it can be assumed that the environmental parameters (temperature, air pressure, gas humidity at the hose entry) will vary neither during a surgical operation, nor from surgical operation to surgical operation.

The invention, therefore, also relates to a method for measuring the water content of a humidifying medium, which is provided in a hose that is passed by a gas, characterized by that a) the heating wire is heated in intervals,
b) the resistance of the heating wire is measured at least at two points of time during the heating interval,
c) from the determined resistances a change in resistance, a time of a change in resistance or a time constant ($T_{100}$, $T_{63}$) is calculated, and
d) from the evaluation of the change in resistance, the time of a change in resistance or the time constant, the water content of the humidifying material is determined.

In a special embodiment of the method, the required time for changing the wire resistance by a defined value (e.g., a change in resistance that corresponds to a change in temperature by 0.1° C., 0.5° C., 1° C., or 2° C.) after activation or deactivation of the heating current is used for determining the water content of the humidifying medium.

In another embodiment of the method, the change in the wire resistance after activation or deactivation of the heating current for a defined duration (e.g. 0.1 s, 0.5 s, 1 s, 2 s, or 5 s) is used for determining the water content of the humidifying medium.

By the method according to the invention, the moisture of the humidifying medium can be measured for the first time with the required accuracy without an additional moisture sensor. In this way, it is possible to activate an alert, when the moisture of the humidifying medium is below a preset threshold value. The preset threshold value may, for instance, be 50%, 40%, 30%, 20%, 10%, or 5% of the maximum moisture. After activation of the alert, the medical operator can, for example, refill water.

Those skilled in the art will be able to employ alternative and/or supplementary embodiments of the invention, without further inventive activity.

The invention claimed is:

1. An insufflation device for use in medical engineering, comprising:
   an insufflator for gas supply and an insufflation hose,
   the insufflation hose including in its interior a humidifying material,
   the humidifying material being in contact with a heating element,
   the heating element being activatable by applying a current,
   the heating element consisting of a wire, the wire changing its resistance with varying temperature of the heating element,
   wherein the insufflator includes a device for measuring the wire resistance, and
   that the insufflator further includes a computing device that determines a water content of the humidifying material from the measured change in resistance of the heating wire during a heating process, wherein a required time $T_{100}$ for changing the wire resistance to its stationary final value after activation or deactivation of the heating current is used for determining the water content of the humidifying material.

2. The device according to claim 1, wherein the currently determined heating wire resistance is processed together with a condition of the heating element (ON/OFF) in a mathematical algorithm, wherein as a result a time constant $T_{63}$ is calculated, wherein this value serves as a measure for the water content of the humidifying material.

3. The device according to claim 1, wherein the determined water content is used for displaying the water content and is used as an alarm for refilling the humidifying material.

4. The device according to claim 1, wherein for the insufflation hose, a set of calibration data is stored on a data carrier that is attached at the hose.

5. A method for measuring water content of a humidifying material, which is provided in a hose that is passed by a gas, wherein
   a) a heating wire is heated in an interval,
   b) the resistance of the heating wire is measured at least at two points of time during the interval,
   c) from the determined resistances, a change in resistance, a time of a change in resistance, or a time constant ($T_{100}$, $T_{63}$) is calculated, and
   d) from the evaluation of the change in resistance, the time of a change in resistance, or the time constant, the water content of the humidifying material is determined, wherein a required time for changing the wire resistance by a defined value after activation or deactivation of a heating current is used for determining the water content of the humidifying material.

6. The method according to claim 5, wherein an alert is triggered, when the water content of the humidifying material is below a preset threshold value.

7. The method according to claim 6, wherein the preset threshold value corresponds to 50%, 40%, 30%, 20%, 10%, or 5% of the maximum moisture.

* * * * *